United States Patent [19]

Weathers et al.

[11] Patent Number: 4,857,464
[45] Date of Patent: Aug. 15, 1989

[54] MIST CULTIVATION OF CELLS

[75] Inventors: Pamela Weathers, Stowe, Mass.; Kenneth Giles, Shepton Malet, England

[73] Assignee: Bio-Rational Technologies, Inc., Worcester, Mass.

[21] Appl. No.: 831,579

[22] Filed: Feb. 21, 1986

[51] Int. Cl.⁴ ............................................. C12N 5/00
[52] U.S. Cl. ........................ 435/240.23; 435/240.45; 435/240.48; 435/240.4; 435/285; 47/59; 47/62
[58] Field of Search .................... 435/240.23, 240.241, 435/240.4, 240.45, 240.48, 284, 285; 47/59-62

[56] References Cited

U.S. PATENT DOCUMENTS 4,332,105  6/1982  Nir .................................... 47/62

FOREIGN PATENT DOCUMENTS 0052001  5/1982  European Pat. Off. ..
59-45873  3/1984  Japan ................................ 435/284
59-45879  3/1984  Japan ................................ 435/284
 323439  2/1972  U.S.S.R. ........................... 435/284

Primary Examiner—Benoit Castel
Attorney, Agent, or Firm—Abelman, Frayne, Rezac & Schwab

[57] ABSTRACT

Cells are cultivated in a chamber having a high nutrient humidity. Gas drives liquid nutrient through devices which produce a fine mist within the chamber. Screens or convoluted mesh supports the cells, and provides for drainage of cell products and media away from the cells for processing. The chamber is sealable to provide for axenic conditions.

5 Claims, 5 Drawing Sheets

MIST CULTIVATION OF CELLS

BACKGROUND OF THE INVENTION

The invention relates to cultivation of cells, and more particularly to tissue propagation and product retrieval under axenic conditions.

The cultivation of cells for metabolic and other products is rapidly gaining in importance, as the laboratory production of these products becomes economically infeasible, or is technologically impossible. Moreover, recombinant DNA techniques and related technologies has made possible the generation of cell lines which can produce more numerous products in heretofore unknown quantities. Accordingly, cultivation of cells and the attainment of high yields is a primary objective for an increasing number of manufacturing enterprises.

Conventional plant tissue culture methods rely on the provision of minerals, growth regulators and a carbon source, usually sucrose, to plant tissue by incorporating these ingredients in an agar solidified gel. Plant tissue is placed on the surface of the gel and nutrients are taken up from the gel. This method of culture has several inherent problems, all of which mitigate against the optimal growth of the plant tissue. Many initial explants and some callus cultures produce and introduce into the medium, compounds which inhibit the growth of the plant tissues by either slowing the cell division rate, or by killing the tissue. Such diffusion necessitates the frequent transfer of the tissue to fresh media, involving both the use of extra medium and its preparation, as well as labor. Since the plant tissue is necessarily growing in close contact with the medium, the maximum availability of oxygen is limited to the upper side of the callus or tissue. This restricts the respiration rates of the lower side of the callus and growth in that region is often depressed. Plant tissue, both differentiated and undifferentiated, produce volatile growth regulators, notably ethylene, which affects the form and growth rate of the tissue. In conventional culture vessels, frequently petri dishes or other plastic or glass containers, these volatile compounds can build up and prejudice the efficient growth of the tissue. Because all the nutrients, growth regulators and carbon sources for the growth of the plant tissue must diffuse through the gelled medium, the growth rate of the tissue is limited by the rate of this diffusion.

Suspension cell culture has been used to alleviate some of the problems in plant culture, and is widely used in the cultivation of many cell types. In plant cell culture, suspension cultures are induced by manipulations of the growth regulator component of the medium to produce embryos. The cultures require regular subculturing and can suffer from depletion of the nutrients or build-up of noxious compounds in the medium if not transferred regularly. Aeration in these cultures is usually provided by agitation of the culture vessel; thus, little control is exercised over water soluble volatile gases such as ethylene. Aeration remains a predominant problem in the culture of all cell types by suspension methods.

Other cultivation methods include multiple plate suspension propagators, glass bead propagators, and tubular spiral films. Multiple plate propagators comprise a number of support layers within a liquid suspension. This system suffers from the same disadvantages as other suspension cultivators, particularly, poor gas diffusion and the accumulation of harmful products within the suspension. Glass bead propagators comprise glass beads coated with cells. The beads provide an increased surface area for cell attachment. Not only does this method fail to solve gas diffusion limitations, but subjects the cells to great mechanical stress, resulting in high cell loss and concomitant low yields. In the use of tubular spiral films or hollow permeable fibers, cells are introduced to the inside of a tube which is permeable to gases. Liquid nutrient is flowed through the inside of the tube. This approach also suffers from diffusion problems, in that cells disposed inward from the lining cells are exposed to increasingly lower amounts of diffused gases.

Accordingly, it is an object of the invention to provide a method and apparatus for the cultivation of cells and tissues. It is a related object to provide for the cultivation of one cell type in axenic conditions.

It is a further object to provide for heretofore unrealized high gas availability to the cultivated cells, as well as the unlimited supply of solubilized nutrients.

It is an additional object to provide for the improved growth of most cell types, including plant cells and hybridomas, by a single apparatus design.

It is yet another object to provide for reduced labor requirements in the cultivation of plant and other tissue types. Further, it is an object to provide highly consistent, repeatable cell cultivation by efficient, low cost apparatus and processes. A related objective is the provision of a cultivating system which is self-adjusting and microprocessor controllable, whereby a minimum amount of human interaction is required for generating high product yields.

SUMMARY OF THE INVENTION

In accomplishing the foregoing and related objects, the invention provides an apparatus for the cultivation of cells, in a nutrient humid environment. Cells are provided with readily available gaseous as well as liquid nutrient supplies. Axenic conditions are provided to enable cultivation of distinct cell lines.

In accordance with one embodiment of the invention, a mist emitting device is disposed within a sealable chamber. Liquid nutrient is supplied from a sealable container to the mist emitting device, where it is driven by pumping or pressurized gas. Mist emitting devices are selected to provide a mist, 0.1 to 10 microns, rather than a spray, 100 to 5000 microns. Results can be obtained, however, with a particle size of 10 to 100 microns (fog), however misting is preferred. Where the liquid is driven by gas, the gas is preferably selected to provide a primary metabolic requirement for the cells. For aerobes, the gas will contain oxygen, while for anaerobes a substitute gas is used, such as nitrogen.

Cells are supported on a biologically inert member. The material is selected for resistance to decay, with its attendant introduction of contaminants. Accordingly, stainless steel and plastics, including Teflon, a trademark of DuPont, have been found suitable. In one embodiment, one or more screens are provided, which support the cells within the chamber.

Coalesced nutrient drains through the support to be collected within a sump area for retrieval of products and reusable media. In another embodiment, a convoluted mesh of biologically inert material provides a large surface area upon which attaching organisms, such as animal cells, may grow.

In accordance with a further aspect of the invention, a sonicating mist emitting device is used, whereby media is prevented from foaming after discharge from the mist emitting device. It has been found, for example, that media with high quantities of protein, such as serum, tend to foam when emitted from conventional mist emitting device apparatus. Sonicating devices, or ultrasound devices, employ sound waves to disperse liquid within a small particle range.

In accordance with yet another aspect of the invention, a source of metabolically utilizable light is provided. The light source may be disposed within or without the chamber, depending on space and absorption considerations.

In accordance with an additional aspect of the invention, a processor, such as a computer microprocessor and associated hardware, monitors and controls process parameters of the apparatus. Solenoids and pressure regulators which are externally adjustable are employed to control liquid and gaseous nutrients, respectively. The processor is programmable to continuously adjust mist emission frequency and duration, humidity, temperature, and other process parameters, as required by the particular organism cultivated. Relatedly, the cell support is provided as a conveyor for moving the cells within the chamber. Accordingly, loading and unloading of cells is automatable, in addition to the foregoing cultivation parameters.

In a yet further embodiment, gas and liquid permeable containers may be installed within the chamber of the invention, whereby the cells are contained for convenient handling, and are provided with additional growth surface area.

BRIEF DESCRIPTION OF THE DRAWINGS

Other aspects of the invention will become apparent after considering several illustrative embodiments taken in conjunction with the drawings in which.

DETAILED DESCRIPTION OF THE INVENTION

With reference to the Figures, a tissue cultivation device in accordance with the invention provides a nutrient rich environment while removing metabolic and waste products in a continuous manner.

Figure 1:
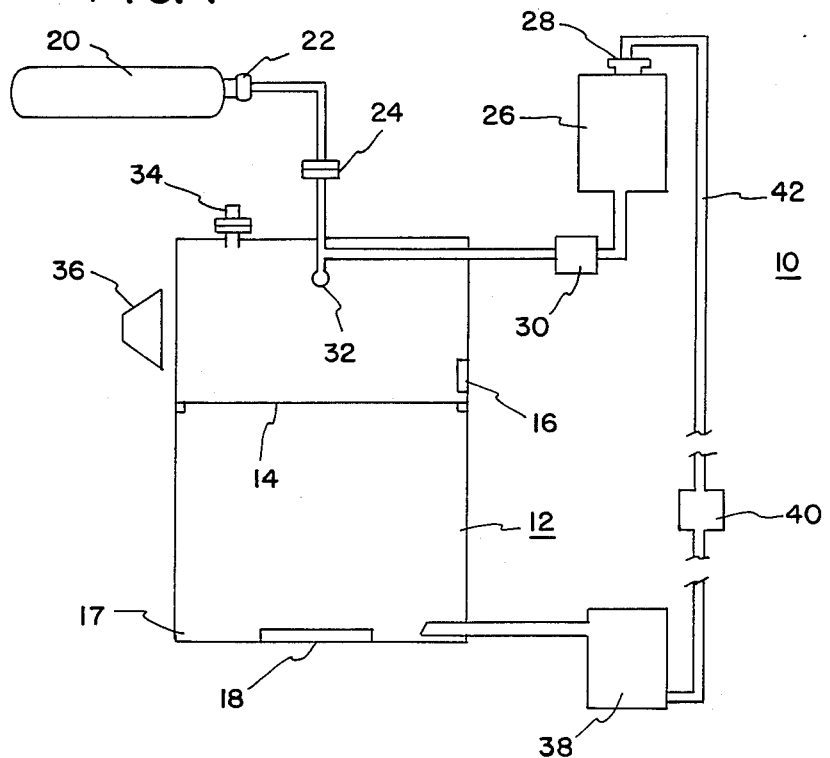
FIG. 1 is a diagrammatic view of a cell cultivation apparatus in accordance with the invention.

Referring to FIG. 1, device 10 includes a growth chamber 12 sealable to maintain axenic conditions. Chamber 12 is advantageously fabricated from glass, plexiglass, or other biologically inert, transparent material. Where it is desired to heat sterilize, glass, polycarbonate, polyamide, and related materials are preferred. A screen 14 of biologically inert material has a mesh or pore size which supports cells while enabling good drainage. A cell loading and recovery port 16 is provided proximate screen 14. A cleaning and sterilizing access port 18 is disposed at the bottom or lower end of chamber 12.

Cellular metabolic requirements are provided in the form of nutrient suspensions and gases. Gas cylinder 20 and regulator 22 provide optimum amounts of the required gases, which may be air, higher oxygen or carbon dioxide concentrations, or for example nitrogen, in the event anaerobes are being cultivated. A filter 24 removes contaminants, including other organisms.

Nutrient solution, or media, is stored in vessel 26. An appropriate lid 28 maintains sterility within vessel 26. A pump 30 may be used, when required, to deliver solution to chamber 12 or mist emitting device 32.

Mist emitting device 32 emits a mist of solution, driven by pressurized gas, or a pump. In a preferred embodiment, droplet size is on the order of 1 to 100 microns. Where the nutrient solution contains proteinaceous material, or other material which would foam in convention misting mist emitting device apparatus, the invention provides a sonicating mist emitting device. This has been found to prevent sparging or foaming of the solution. A positive pressure is fostered within the chamber due to the sealed nature of same. A filtered gas outlet 34 is provided to relieve most pressure, however a slight overpressure is advantageously maintained to preserve axenic conditions. Although gas cylinder 20 may not be required for all cell types, it is advantageously used for this purpose.

Light source 36 is provided as required for plant cell metabolism. Light source 36 may alternatively be mounted within chamber 12.

Collection of secondary metabolites as part of spent nutrient fluid effluent occurs within the lower region of chamber 12. Liquid passes to a product storage vessel 38, and is processed at 40. In processing, collected target products are separated, and cell toxins are removed where economically feasible. Reusable media is replaced to storage vessel 26 via conduit 42.

Figure 2:
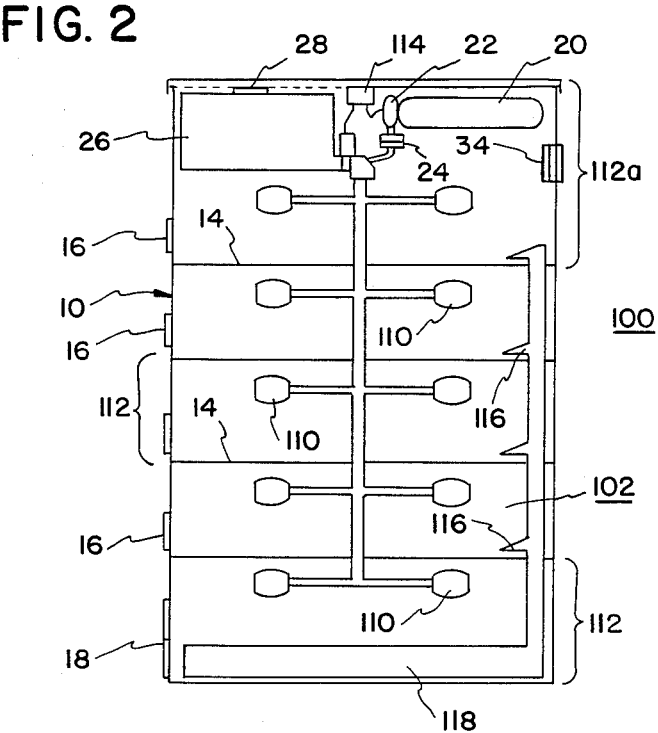
FIG. 2 is a diagrammatic view of a multiple support apparatus in accordance with the invention.

A self-contained apparatus 100 in accordance with the invention is shown in FIG. 2. A chamber 102 houses a plurality of mist emitting devices 110 in a plurality of separated chambers 112. Chamber 112a contains nutrient reservoir 26 and gas cylinder 20, as well as corresponding elements as described above, similarly identified. Apparatus 100 further includes electronic controller 114 for remote activation of nutrient and gas supplies, as by a microprocessor. Drainage collectors 116 conduct liquid to collecting vessel 118, where materials are retrieved, optionally processed, and reused where appropriate.

Figure 3:
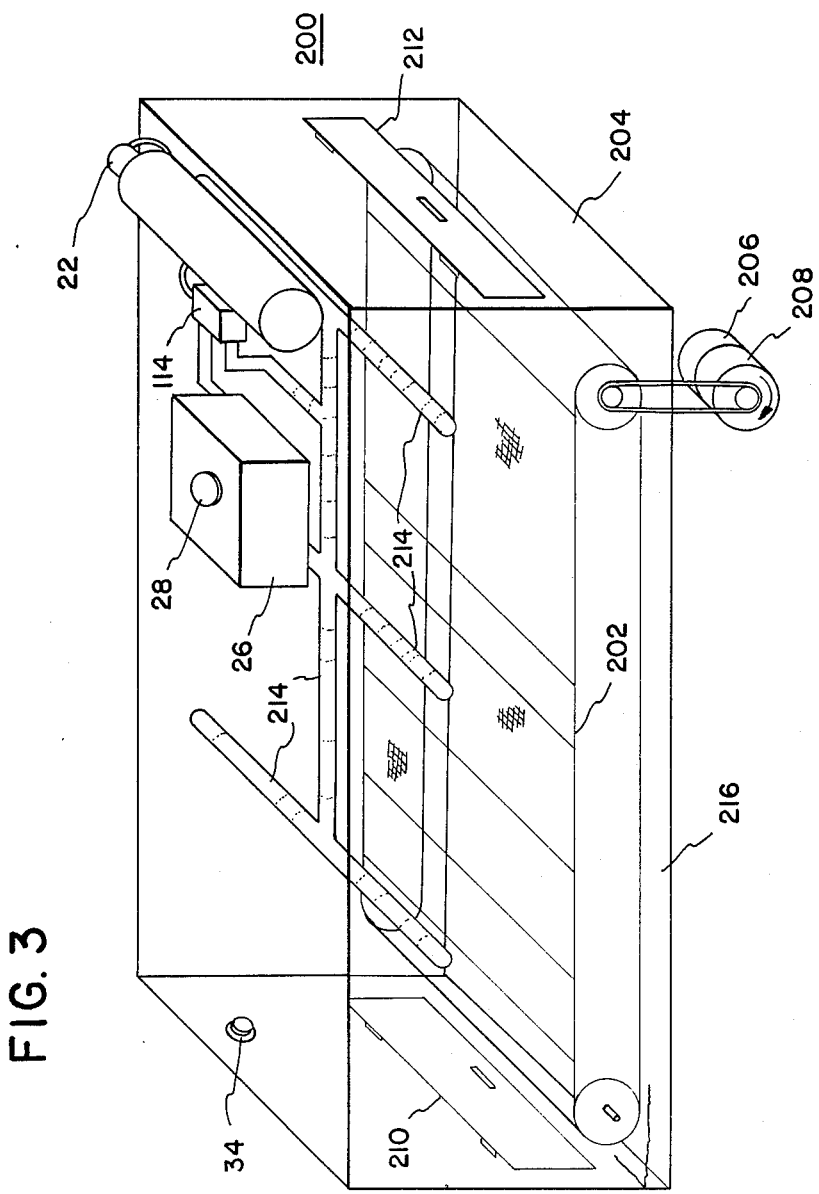
FIG. 3 is a perspective view of an alternative apparatus in accordance with the invention, illustrating an internalized conveyor apparatus.

An alternative embodiment 200 of the invention is shown in FIG. 3. A mesh conveyor belt 202 is fabricated of inert material, and travels within an enclosure 204. Motor 206 and gear reducer 208 drive belt 202 at a slow rate, whereby new cells are added at loading port 210 and removed at unloading port 212. Nutrient supply is provided, as discussed above, and is delivered through misting apertures 214. Alternatively, a plurality of ultrasonic mist emitting devices may be attached.

Figure 4:
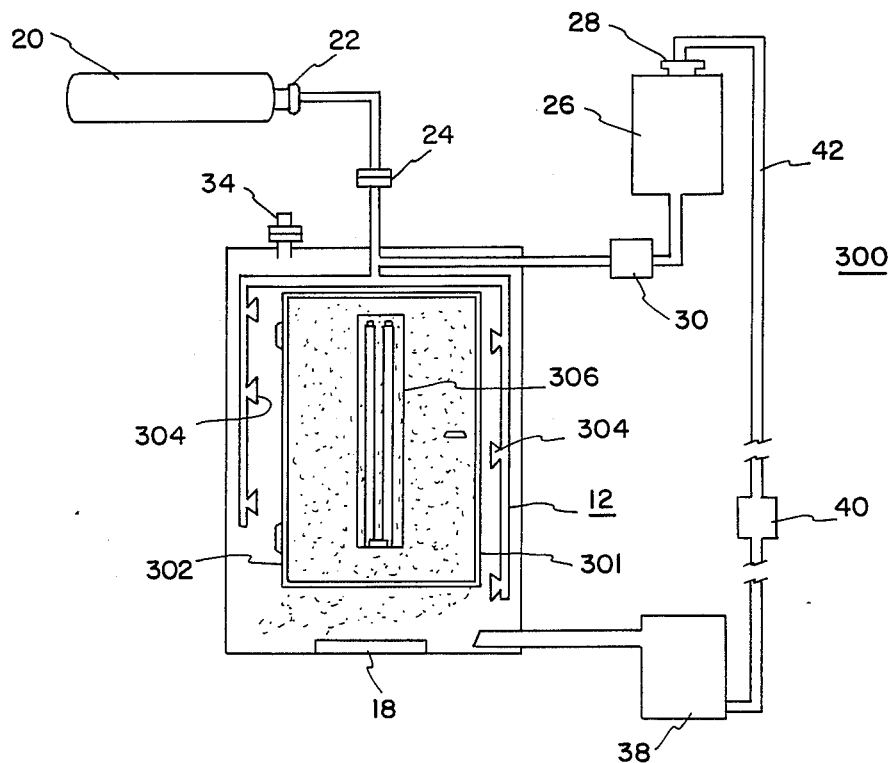
FIG. 4 is a diagrammatic view of an alternative apparatus in accordance with the invention, showing convoluted mesh support, and internally disposed light source.

FIG. 4 illustrates an alternative cultivator 300 useful for organisms which require support for attachment, which is necessary for growth. A convoluted mesh 301 of inert material, such as nylon or polypropylene, serves as the cell support. The mesh is innoculated by passage through a solution containing cells. To promote attachment, a biological "adhesive", such as poly lysine, is sprayed onto the mesh. Cells may alternatively be covalently bonded to a cellulosic support. Cells are recovered or removed by shocking with any of the numerous known compounds, such as trypsin, for hybridomas, which cause release. A larger access port 302 facilitates loading and removal of the convoluted mesh support matrix. Mist emitting devices 304 are disposed in a manner which minimizes mesh interference, while providing for high nutrient distribution. Light source 306 is disposed within chamber 12. In the embodiment shown in FIG. 4, mesh 301 can be wrapped about a centrally disposed light source. Light source 306 is advantageously removable to facilitate mesh 301 insertion and removal.

In accordance with the invention, cells and tissues are cultivated to produce useful products in high yields, at low cost. Cells are grown in an environment of high humidity, rich in nutrients. The embodiments are sealed to provide sterile conditions, thus freeing the cultures from antagonists and competition.

In the prior art, plant tissue cultures are grown on a solid nutrient support. As the plant cells metabolize, toxins are produced, whereby the media loses suitability for growth. The instant invention avoids the necessity of transplanting cells onto fresh media support, by providing for the drainage of accumulated media and products, as well as of toxins, away from the cells. Accordingly, cells may be cultivated to the desired point, for example, until plantlets are formed, without the laborious and wasteful task of repeated transplanting.

Figure 5:
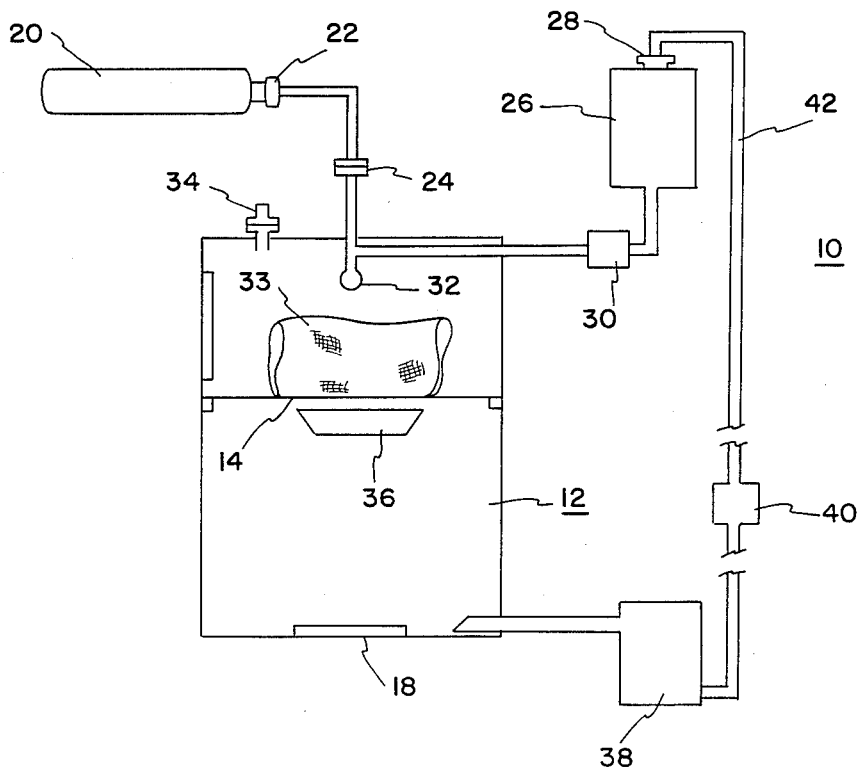
FIG. 5 illustrates a permeable cell support pillow, in accordance with the invention, supported within the apparatus for FIG. 1.

The invention provides for the cultivation of all cell types, including anaerobes. Fine screens 14 may be used for attaching and non-attaching cells, including hybridomas. Additionally, the apparatus of the invention may be used in combination with alternative cell support structures. As can be seen in FIG. 5, a pillow-like device 33 permits passage of gases and nutrients, yet is sealed to prevent escape of cells.

A primary problem in suspension cell cultures is the oxygen transfer rate between the liquid suspension and the ambient atmosphere. The present invention eliminates this problem by surrounding the cells in a highly nutrient saturated atmosphere. It is of paramount importance, in the practice of the invention, that the cells are not sprayed with nutrient. Spraying would introduce droplets large enough to create a contiguous liquid interface, which would act as an oxygen depletion barrier. In accordance with the invention, droplets may ultimately form at various locations, however, the cells are in atmosphere of high saturation, not nutrient coating. Accordingly, cells are well oxygenated at all times. A further advantage is that nutrients need not diffuse through a gelled solid support, and thus are available to the full extent required by the cells.

An additional advantage of the invention is the facile removal of secondary metabolites. As the cells are supported above a sump area 17,118,216 accumulated run-off can be reintroduced in whole or in part, depending on the metabolism of the organism.

A further advantage of the present invention is a sharp reduction in labor. As described above, tissue does not require transfer. Moreover, all operating parameters are readily adapted to microprocessor control, thus further reducing labor input, while enhancing consistency. An apparatus is herein provided which requires only that cell innoculum is added at one end of a conveyor, (202) and product is removed at the other end. A plurality of conveyors may be housed within one chamber 204 for increased product yield.

Tables 1 and 2 illustrate test results obtained in a comparison cultivation of cells using the apparatus of FIG. 1 and prior art agar plating, of plant tissue callus. Standard aseptic preparation of the apparatus of the invention was accomplished by sequentially rinsing the apparatus with hypochlorite solution, ethanol, and sterile distilled water. The unit was then placed under a laminar flow hood and allowed to dry for 8 hours. A standard stock solution of M+S medium containing 0.1 ppm 2,4-D was prepared, placed in the medium tank and then autoclaved for 20 minutes at 15 lbs. pressure. Uniform carrot callus sections were cut from existing cultures by means of a sterile cork borer. Each specimen was individually weighed on sterile petri dishes of known mass.

Media in the apparatus was introduced at a rate of 0.5 ml per hour in single five second bursts. At the conclusion of the experiment, which lasted for the duration of three weeks, the calli were removed, individually weighed and recorded for final evaluation. The data obtained as a result of the weighing is provided in Table 1.

A total of 16 carrot callus cores were taken, individually weighed, and assigned a specific location either in the apparatus or on an agar petri dish containing identical medium. The weights and relative positions of the cores were recorded at the onset of the experiment and are given in Table 1.

The overall results of the experiment are depicted in Table 2. There was an apparent mean growth of 28% for the callus cultured in the apparatus and a mean rate of 8% for the samples placed on agar.

Overall, the callus in the apparatus grew 3.5 times as much as the control. In addition, there was an obvious difference in the general appearance of the two sets of callus at the conclusion of the experiment. The callus in the apparatus exhibited a bulbous, almost spherical growth of new tissue. In contrast, the agar culture showed a rather erratic, knobby pattern of growth.

TABLE 1

| | CALLUS GROWTH | | | |
|---|---|---|---|---|
| # | APPARATUS 1 | APPARATUS 2 | AGAR 1 | AGAR 2 |
| 1 | 624 | 788 | 638 | 671 |
| 2 | 581 | 765 | 662 | — |
| 3 | 650 | 811 | 597 | — |
| 4 | 600 | 762 | 671 | 751 |
| 5 | 605 | 767 | 613 | 655 |
| 6 | 562 | 761 | 682 | 742 |
| 7 | 646 | 801 | 643 | 683 |
| 8 | 622 | 773 | 625 | 633 |
| MEAN | 611 | 779 | 641 | 689 |
| SD | 31 | 19 | 29 | 48 |

Actual numerical results and statistical measures of each callus. Blanks in the final agar column are of two calli that showed incomplete data. Units in Tables 1 and 2 are grams × 10 to the minus fourth.

INITIAL WEIGHT V. FINAL WEIGHT:
TISSUE CULTIVATION APPARATUS OF FIG. 1 (CX);
PRIOR ART AGAR PLATING (AX)

TABLE 1-continued

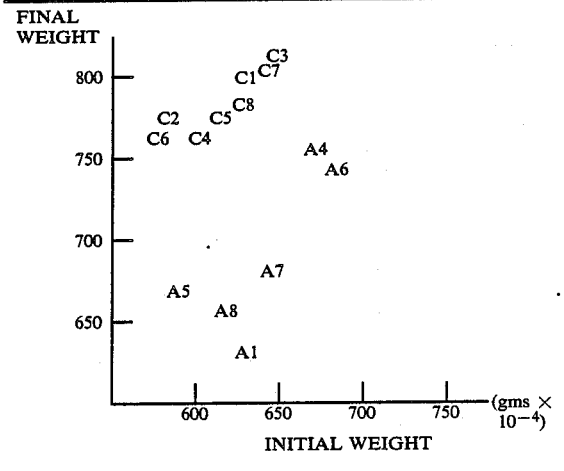

The present invention is distinguished from hydroponics in a number of significant respects. U.S. Pat. No. 4,332,105 to Nir may be taken as a representative example of hydroponic type plant cultivation. The devices of hydroponics are designed to accommodate differentiated tissue, wherein a whole plant organism includes roots and leaves, each treated in a different manner. The invention cultivates undifferentiated tissues which cannot be cultivated by hydroponic methods requiring roots or other such differentiated type structures. Additionally, hydroponic devices do not provide for collection of secondary metabolites, an important benefit provided by the instant invention. Additionally, among other aspects which prohibit their use in cell or undifferentiated tissue cultivation, these prior art devices do not provide for axenic growth; gas selection and control; precise temperature regulation; or misting, where the environment is devoid of spraying or significant liquid deposits.

While various aspects of the invention have been set forth by the drawings and the specification, it is to be understood that the foregoing detailed description is for illustration only and that various changes in parts, as well as the substitution of equivalent constituents for those shown and described, may be made without departing from the spirit and scope of the invention as set forth in the appended claims.

What is claimed is:

1. A method of cultivating cells, said cells originating from plants, animals and microbes in both a differentiated and undifferentiated state, comprising:
    (a) supporting the cells on a liquid and gas permeable member;
    (b) supporting the member within a sealable container;
    (c) misting a liquid nutrient with droplets having a droplet size of between about 0.1 and about 10 microns into the chamber to provide a nutrient humid environment.
2. Method of claim 1, further comprising the step of:
    (d) introducing a gas into the sealable container.
3. Method of claim 2, further comprising the step of:
    (e) controlling entry of gas and nutrients with a processor and associated hardware.
4. Method of claim 1, wherein in step (a) the liquid and gas permeable member is a screen of biologically inert material.
5. Method of claim 1, wherein in step (a) the liquid and gas permeable member is a convoluted mesh of biologically inert material.

* * * * *